ized Patent [19]

United States Patent [19]

Lagow

[11] Patent Number: 5,075,509
[45] Date of Patent: Dec. 24, 1991

[54] FLUORINATION OF ORTHOCARBONATES AND POLYALKOXY PROPANES

[75] Inventor: Richard J. Lagow, Austin, Tex.

[73] Assignee: Exfluor Research Corporation, Austin, Tex.

[21] Appl. No.: 386,957

[22] Filed: Jul. 28, 1989

Related U.S. Application Data

[60] Division of Ser. No. 368,130, Jun. 16, 1989, which is a continuation of Ser. No. 90,658, Aug. 18, 1987, abandoned.

[51] Int. Cl.$^5$ .................... C07C 43/30; C07C 43/313
[52] U.S. Cl. ...................................... 568/603; 568/604
[58] Field of Search ................................. 568/603, 604

[56] References Cited

U.S. PATENT DOCUMENTS 2,611,787  9/1952  Holm .
3,226,418  12/1965  Anderson et al. .
3,415,847  12/1968  Talbott .
4,113,435  9/1978  Lagow et al. .

FOREIGN PATENT DOCUMENTS

WO87/02994  5/1981  World Int. Prop. O. .

OTHER PUBLICATIONS

Adcock et al., *J. Org. Chem.* 40:3271 (1975).
Persico et al., *J. Am. Chem. Soc.* 107:1197 (1985).
Aymonino, *Chem. Commun.* 241 (1965).
Varetti and Aymonino, *Chem. Commun.* 680 (1967).
Tarrant and Brown, *J. Am. Chem. Soc.* 73:1781 (1951).
Lagow and Margrave, *Prog. of Inorg. Chem.* 26:161 (1979).
Couch et al., *Chem. Commun.* 91 (1971).
DeMarco et al., *J. Org. Chem.* 37:3332 (1972).
Majid and Shreeve, *J. Org. Chem.* 38:4028 (1973).
Redwood et al., *Can. J. Chem.* 43:1893 (1965).
Redwood et al., *Can. J. Chem.* 45:389 (1967).
Adcock, J. L. and M. L. Robin, *Government Report* ADA 139987 (1984).
International Preliminary Examination Report for the Corresponding PCT Application.

*Primary Examiner*—Howard T. Mars
*Attorney, Agent, or Firm*—Hamilton, Brook, Smith, & Reynolds

[57] ABSTRACT

Perfluoroalkylorthocarbonates and perfluoropolyalkoxypropanes are disclosed. The perfluoro compounds are synthesized by direct fluorination procedures. The perfluoro compounds are useful lubricants, heat exchangers, vapor phase soldering fluids, solvents, and oxygen carriers.

4 Claims, 2 Drawing Sheets

TETRAMETHYL
ORTHOCARBONATE            49.5%

TETRAETHYL
ORTHOCARBONATE            56.5%

TETRA -I- PROPYL
ORTHOCARBONATE       BOTH ISOMERS ARE INSEPARABLE
                           (YIELD 12.8%)

1,1,3,3-TETRAMETHOXY PROPANE     46.8%            13.7%

1,1,3,3-TETRAETHOXY PROPANE            13.0%

23.4%

20.0%

9.3%

FLUORINATION OF ORTHOCARBONATES AND POLYALKOXY PROPANES

GOVERNMENT SUPPORT

This invention was made with government support under grant AFOSR-87-0016 awarded by the Air Force and grant NAG3-602 awarded by the National Aeronautics and Space Administration. The government has certain rights in this invention.

This application is a division, of application Ser. No. 07/368,130, filed June 16, 1989 which is a file wrapper continuation of application Ser. No. 07/090,658, filed Aug. 18, 1987 now abandoned.

BACKGROUND

The difficulty with the synthesis of perfluoro esters lies in instability of the ester linkage toward hydrogen fluoride and the facile dissociation of perfluoro esters by nucleophilic attack. The electrolytic fluorination of esters is precluded because they are spontaneously decomposed in the acidic solution. The direct fluorination of ethyl acetate (See Adcock, J. L. et al., *J. Org. Chem.* 40, 3271 (1975)) represents the first successful fluorination of an ester, giving $CF_3COOCF_2CF_3$ and $CF_3COOCHFCF_3$ in 5% and 20% yield respectively. Extension of this direct fluorination technique has previously led to the conversion of hydrocarbon polyesters to highly fluorinated polyesters, which are important precursors to perfluoropolyethers. Persico, D. F. et al., *J. Am. Chem. Soc.* 107, 1197 (1985).

There were few reports of the preparation of perfluoroesters by indirect methods. The first reported reactions were the dimerization and trimerization of $COF_2$ to yield $FCO_2CF_3$ and $(CF_3O)_2CO$ respectively. Photolysis reaction of $CF_3OF$ and $CF_3OOCF_3$ in the presence of CO resulted in the same products as above reactions. Aymonino, P. J., *Chem. Commun.* 241 (1965); Varetti, E. L. and Aymonino, P. J., *Chem. Commun.* 680 (1967). A more general synthesis is the low temperature reaction of perfluoroacyl fluorides with perfluoro alkoxide salts.

With the execption of the reaction of fluoroesters $R_fCOOCH_3$ with dimethyl sulfone to yield ortho esters $R_fC(OCH_3)_3$ (Holm, T., U.S. Pat. No. 2,611,787 (1952)) and the isolation of $CHFClC(OC_2H_5)_3$ by Tarrant and Brown (Tarrant, P. and Brown, H. A., *J. Am. Chem. Soc.* 73, 1781 (1951)) little synthetic information on fluorinated ortho esters has appeared in the literature.

SUMMARY OF THE INVENTION

This invention pertains to perfluoroalkyl orthocarbonates and perfluoropolyalkoxypropanes and to methods of producing these perfluorinated compounds.

The perfluoroalkyoorthocarbonates are represented by the formula:

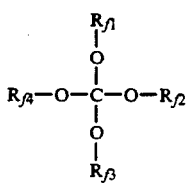

wherein $R_{f1}$, $R_{f2}$, $R_{f3}$ and $R_{f4}$ are the same or different short, straight or branched chain perfluoroalkyl radicals. In preferred embodiments, $R_{f1}$, $R_{f2}$, $R_{f3}$ and $R_{f4}$ are the same or different and are selected from $-CF_3$, $-CF_2CF_3$, $-CF_2CF_2CF_3$, $-CF(CF_3)_2$, $-CF_2CF_2CF_2CF_3$, $-CF(CF_3)CF_2CF_3$, $-CF_2CF(CF_3)_2$, and $-C(CF_3)_3$.

The perfluoroalkoxypropanes are represented by the formula:

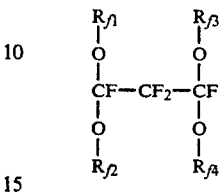

wherein $R_{f1}$, $R_{f2}$, $R_{f3}$ and $R_{f4}$ are short, straight or branched chain perfluoroalkyl radicals. In preferred embodiments, $R_{f1}$, $R_{f2}$, $R_{f3}$ and $R_{f4}$ are the same or different and are selected from $-CF_3$, $-CF_2CF_3$, $-CF_2CF_2CF_3$, $-CF(CF_3)_2$, $-CF_2CF_2CF_2CF_3$, $-CF(CF_3)CF_2CF_3$, $-CF_2CF(CF_3)_2$, and $-C(CF_3)_3$.

The perfluoroalkylorthocarbonates and perfluoroalkoxypropanes of this invention are produced by direct fluorination with elemental fluorine. The perfluoro compounds are more volatile than perfluoropolyethers of the same molecular weight. They are unaffected by concentrated sulfuric acid and nitric acid, but decompose in hydrogen fluoride solution and concentrated hydrochloric acid. They are stable at 150° C. and above. The perfluoro compounds of this invention are useful as lubricants, heat exchangers, solvents, vapor phase soldering fluids and oxygen carriers.

DETAILED DESCRIPTION OF THE INVENTION

Figure 1:
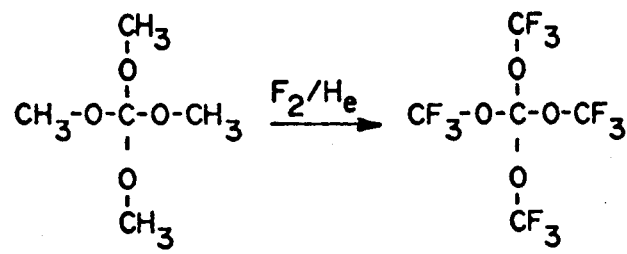
FIG. 1 shows the reactions of elemental fluorine in the production of perfluoroalkylorthocarbonates and perfluoroalkyoxypropanes.
Figure 1:
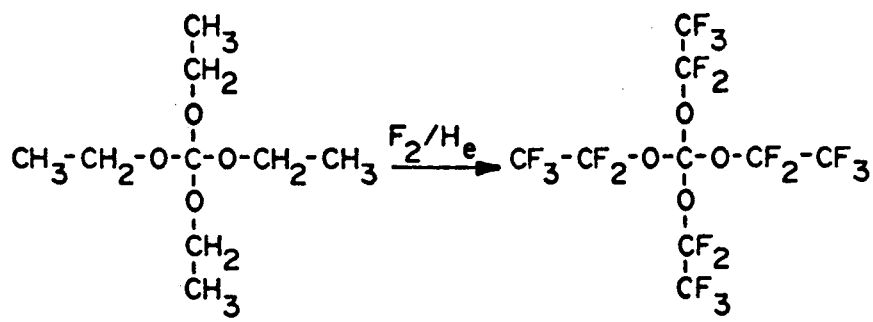
Figure 1:
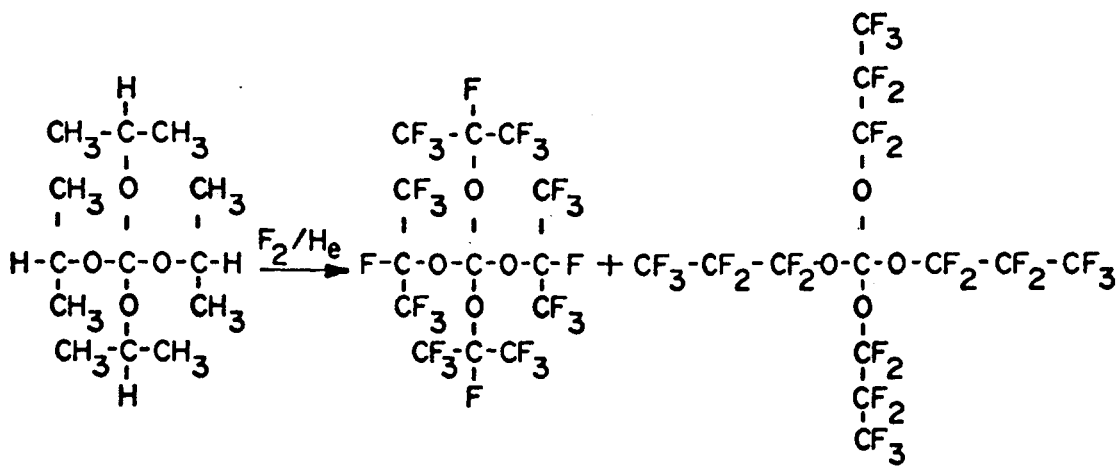
Figure 1:
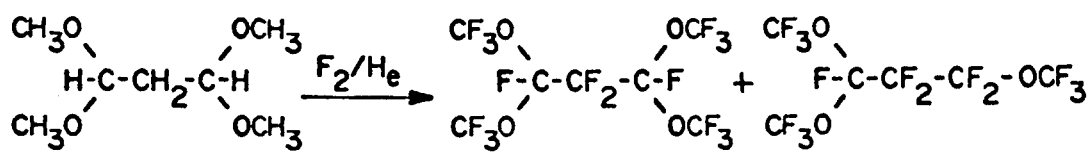
Figure 1:
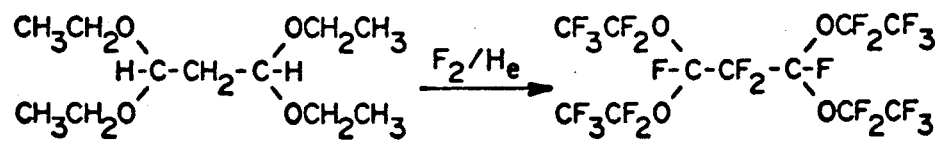
Figure 1:
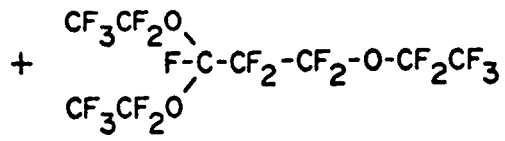
Figure 1:
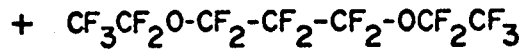
Figure 1:
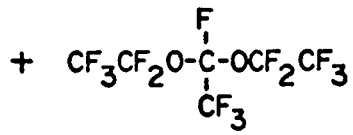

The perfluoroalkylorthocarbonate of this invention are represented by the formula:

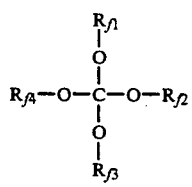

wherein $R_{f1}$, $R_{f2}$, $R_{f3}$ and $R_{f4}$ are the same or different and are selected from short, straight or branched chain perfluoroalkyl radicals. In preferred embodiments, $R_{f1}$, $R_{f2}$, $R_{f3}$ and $R_{f4}$ are selected from $-CF_3$, $-CF_2CF_3$, $-CF_2CF_2CF_3$, $-CF(CF_3)_2$, $-CF_2CF_2CF_2CF_3$, $-CF(CF_3)CF_2CF_3$, $-CF_2CF(CF_3)_2$, and $-C(CF_3)_3$. Especially preferred perfluoroalkylorthocarbonates are represented by the formula:

$$C(OR_f)_4$$

wherein $R_f$ is selected from $-CF_3$, $-CF_2CF_3$, $CF_2CF_2CF_3$ and $CF(CF_3)_2$.

The perfluoroalkyoxypropanes of this invention are represented by the formula:

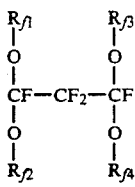

wherein $R_{f1}$, $R_{f2}$, $R_{f3}$ and $R_{f4}$ are short, straight or branched chain perfluoroalkyl radicals. In preferred embodiments, $R_{f1}$, $R_{f2}$, $R_{f3}$ and $R_{f4}$ are selected from $-CF_3$, $-CF_2CF_3$, $-CF_2CF_2CF_3$, $-CF(CF_3)_2$, and $-CF_2CF_2CF_2CF_3$, $-CF(CF_3)CF_2CF_3$, $-CF_2CF(CF_3)_2$, $-C(CF_3)_3$. Especially preferred perfluoroalkyoxypropanes are represented by the formula:

wherein $R_f$ is selected from $-CF_3$, $-CF_2CF_3$, $CF_2CF_2CF_3$ and $-CF(CF_3)_2$. In addition, the fluorination procedures for production of perfluoroalkoxy propanes can yield novel compounds of the formula:

wherein $R_f$ is as defined above.

The perfluoro compounds of this invention are produced by the direct fluorination technique of Lagow and Margrave, Prog. of Inorg. Chem. 26, 161: (1979). Appropriate orthocarbonate or polyalkoxypropane starting materials are selected. For example, orthocarbonates can be selected from compounds of the formula:

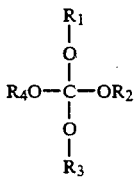

wherein $R_1$, $R_2$, $R_3$ and $R_4$ can be the same or different and are selected from $-CH_3$, $-CH_2CH_3$, $-CH_2CH_2CH_3$, $-CH(CH_3)_2$, $-CH_2CH_2CH_2CH_3$, $-CH(CH_3)CH_2CH_3$, $-CH_2CH(CH_3)_2$, and $-C(CH_3)_3$. Polyalkoxypropanes can be selected from compounds of the formula:

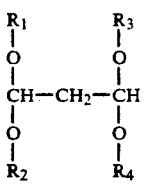

wherein $R_1$, $R_2$, $R_3$ and $R_4$ can be the same or different and are selected from $-CH_3$, $-CH_2CH_3$, $-CH_2CH_2CH_3$, $-CH(CH_3)_2$, $-CH_2CH_2CH_2CH_3$, $-CH(CH_3)CH_2CH_3$, $-CH_2CH(CH_3)_2$, and $-C(CH_3)_3$.

The starting material is placed in a fluorine reactor such as the reactor described by Lagow and Margrave, supra. The reactor is cooled and flushed with an inert gas such as helium or nitrogen after which the fluorine is initiated under controlled conditions. Typically, low fluorine concentrations between about one and about ten percent are used initially. The dilute fluorine is passed over the material to be fluorinated. As the fluorination reaction proceeds the fluorine concentration and flow rate of the gas are gradually increased until pure fluorine conditions are achieved and the material is perfluorinated.

The best results are obtained when the fluorination is performed in the presence of a hydrogen fluoride scavenger such as sodium fluoride as described in U.S. patent application Ser. No. 924,198, entitled "Perfluorination of Ethers in the Presence of Hydrogen Fluoride Scavengers", filed Oct. 27, 1986, the teachings of which are incorporated herein. The presence of a hydrogen fluoride scavenger allows the use of more severe fluorination conditions in this direct fluorination procedure, that is, higher fluorine concentrations and faster rates of fluorine delivery can be used in the presence of a hydrogen fluoride scavenger than can be used in the absence of a scavenger. For example, initial fluorine levels of over 15% and up to 25% and fluorine flow rates of over 8 cc/min/gram of starting material can be used.

In addition, the yield and quality of the perfluoropolyether product is improved when fluorination is conducted in the presence of a hydrogen fluoride scavenger. The scavenger is believed to prevent the formation of ether-HF acid base complexes during the fluorination reaction.

Fluorination in the presence of a hydrogen fluoride scavenger can be performed in several ways. In the preferred mode, the hydrogen fluoride scavenger (in powdered or pellet form) is mixed with the orthocarbonate or polyalkoxypropane. The blend is placed in a suitable fluorination reactor and fluorinated by exposure to gradually increasing concentrations of fluorine gas. Alternatively, the orthocarbonate or polyalkoxypropane may be coated onto the scavenger and fluorinated in this form.

The perfluoroalkyorthocarbonates and perfluoroalkoxypropanes of this invention are useful as lubricants, heat exchangers, vapor phase soldering fluids, solvents and oxygen carriers. For example, the oils are useful as vacuum pump oils and oils for diffusion pumps. The more volatile orthocarbonates and alkoxypropanes are used to cool electronic devices such as computers. The perfluoro compounds are also useful as perfluorocarbon solvents, as oxygen carriers in biomedical applications and as oxygen carriers for organic oxidation reactions.

This invention is illustrated further by the following examples.

EXAMPLES

Tetramethyl orthocarbonate, tetraethyl orthocarbonate, tetra-i-propyl orthocarbonate, 1,1,3,3-tetramethoxypropane, and 1,1,3,3-tetraethoxypropane were used as received from Aldrich Chemicals. Fluorine was research grade and obtained from air Products and Chemicals, Inc. Elemental analyses were performed by E+R Mecroanalytical Laboratory, Inc., Corona, N.Y. $^{19}F$ nmr spectra were recorded on a Varian EM 390 spectrometer operating at 84.67 MHz. Chemical shifts were reported relative to $CFCl_3$. Negative shifts refer to high field of the reference. Mass spectra were measured in a gas phase on a Bell & Howell Model 21-490 mass spectrometer. A Bendix 2300 gas chromatograph equipped with a cryogenic controller and a thermalconductivity detector was used for separation. Infrared spectra were recorded on a Beckman Acculab 8 spectrometer utilizing a gas cell with KBr windows.

In a typical reaction, a mixture of measured amounts of starting material with approximately 10 grams of powdered NaF was packed in a 5 in. × 1 in. copper tube, which was then placed in the first zone of the four-zone cryogenic reactor described previously. Lagow, R. J. and Margrave, J. L., *Prog. Inorg. Chem.* 26, 161 (1979). The last three zones were packed with fluorinated copper turnings. After all zones were cooled to −100° C. for two hours the system was flushed with helium for ten hours. The fluorination was then initiated under controlled conditions. As reactions was completed, the products were fractionated into −78°, −131°, and −196° C. on a vacuum line. Final purification was done by gas chromatography using a fluorosilicone column.

Fluorination of 1,1,3,3-tetramethoxypropane

A 1.49 g of 1,1,3,3-tetramethoxypropane was fluorinated using the conditions as shown in Table 1. The crude product weighing 2.53 g was obtained in the −78° C. trap. Gas chromatographic separation of this portion (0° C. for 10 min., 5° C./min. to 10° C. for 15 min., 10° C./min. to 90° C. for 10 min.) gave perfluoro 1,1,3,3-tetramethoxy propane (1.92 g, 46.8%), and perfluoro 1,1,3-trimethoxy propane (0.48 g, 13.7%).

Perfluoro 1,1,3,3-tetramethoxypropane, bp. 93° C. Anal. Calcd. for $C_7F_{16}O_4$: C, 18.60; F, 69.24. Found: C, 18.50; F, 66.97. MS, m/e(fragment ion): 433 ($C_7F_{15}O_4$, P-F), 367 ($C_6F_{13}O_3$, P-$OCF_3$), 279 ($C_5F_9O_3$), 213 ($C_4F_7O_2$), 201 ($C_3F_7O_2$), 191 ($C_4F_5O_3$), 185 ($C_3F_7O$), 163 ($C_3F_5O_2$), 135 ($C_2F_5O$), 125 ($C_3F_3O_2$), 97 ($C_2F_3O$), 78 ($C_2F_2O$), 69 ($CF_3$, base peak), 50 ($CF_2$), 47 (CFO). IR: 1300 (vs, br), 1240 (vs, br), 1130 (vs, br), 1020 (w), 892 (m), 865 (m), 795 (m), 725 (m) cm$^{-1}$. The FNMR data were reported in Table 5.

Perfluoro 1,1,3-trimethoxypropane, bp. 75° C. Anal. Calcd. for $C_6F_{14}O_2$: C, 18.67; F, 68.90. Found: C, 18.21; F, 68.29. MS, m/e(fragment ion): 367 ($C_6F_{13}O_2$, P-F), 301 ($C_5F_{11}O_2$, P-$OCF_3$), 213 ($C_4F_7O_2$, base peak), 201 ($C_3F_7O_2$), 185 ($C_3F_7O$), 163 ($C_3F_5O_2$), 147 ($C_3F_5O$), 135 ($C_2F_5O$), 125 ($C_3F_3O$), 119 ($C_2F_5$), 113 ($C_2F_3O_2$), 100 ($C_2F_4$), 97 ($C_2F_3O$), 78 ($C_2F_2O$), 69 ($CF_3$), 50 ($CF_2$), 47 (CFO). IR: 1320 (vs), 1250 (vs, br), 1150 (vs, br), 1020 (m, sh), 1004 (m, sh), 918 (w), 822 (m), 800 (m), 720 (m) cm$^{-1}$. The FNMR data were reported in Table 5.

Fluorination of 1,1,3,3-tetraethoxy propane

A 1.82 g of 1,1,3,3-tetraethoxypropane was fluorinated using the same conditions as those for 1,1,3,3-tetramethoxypropane. After fractionation 2.72 grams of crude products were collected. From GC separation at 25° C. were isolated perfluoro 1,1,3,3-tetraethoxypropane (a), perfluoro-1,1,3-triethoxypropane (b), perfluoro-1,3-diethoxypropane (c), and perfluoro-1,1-diethoxypropane (d). The yields were 13.0%, 23.4%, 20.0%, and 9.3% respectively, based on the starting 1,1,3,3-tetraethoxy propane. GC retention time increased in the order: d<c<b<a.

Perfluoro-1,1,3,3-tetraethoxypropane, bp. 143° C. Anal. Calcd. for $C_{11}F_{24}O_4$: C, 20.26; F, 69.92. Found: C, 20.04; F, 69.63. MS, m/e(fragment ion): 517 ($C_9F_{19}O_3$, P-$OC_2F_5$), 301 ($C_5F_{11}O_2$), 263 ($C_5F_9O_2$), 235 ($C_4F_9O$), 119 ($C_2F_5$, base peak), 100 ($C_2F_4$), 97 ($C_2F_3O$), 69 ($CF_3$), 50 ($CF_2$). IR: 1284 (s), 1230 (vs, br), 1150 (vs, br), 1090 (vs), 974 (m, sh), 835 (m), 746 (s, sh), 728 (s, sh), 704 (s, sh) cm$^{-1}$. The FNMR data were reported in Table 5.

Perfluoro-1,1,3-triethoxypropane, bp. 115° C. Anal. Calcd. for $C_9F_{20}O_3$: C, 20.17; F, 70.88. Found: C, 19.86; F, 70.55. MS, m/e(fragment ion): 401 ($C_7F_{15}O_2$, P-$OC_2F_5$), 301 ($C_5F_{11}O_2$), 263 ($C_5F_9O_2$), 235 ($C_4F_9O$), 185 ($C_3F_7O$), 147 ($C_3F_5O$), 119 ($C_2F_5$, base peak), 100 ($C_2F_4$), 97 ($C_2F_3O$), 69 ($CF_3$), 50 ($CF_2$), 47 (CFO). IR: 1300 (s), 1220 (vs, sh), 1135 (vs, br), 1090 (vs), 980 (m, sh), 724 (s, sh), 705 (s, sh) cm$^{-1}$. The FNMR data were reproted in Table 5.

Perfluoro-1,3-diethoxypropane, bp. 77° C. Anal. Calcd. for $C_7F_{16}O_2$: C, 20.02; F, 72.37. Found: C, 19.65; F, 72.17. MS, m/e(fragment ion): 401 ($C_7F_{15}O_2$, P-F), 285 ($C_5F_{11}O$), 263 ($C_5F_9O_2$), 235 ($C_4F_9O$), 185 ($C_3F_7O$), 169 ($C_3F_7$), 147 ($C_3F_5O$), 119 ($C_2F_5$, base peak), 100 ($C_2F_4$), 97 ($C_2F_3O$), 69 ($CF_3$), 50 ($CF_2$), 47 (CFO). IR: 1330 (s, sh), 1230 (vs, sh), 1150 (vs, br), 1100 (vs, sh), 994 (s, sh), 730 (s, sh), 718 (s, sh) cm$^{-1}$. The FNMR data were reported in Table 5.

Perfluoro-1,1-diethoxyethane, bp. 53° C. Anal. Calcd. for $C_6F_{14}O_2$: C, 19.48; F, 71.88. Found: C, 19.20; F, 71.44. MS, m/e(fragment ion): 301 ($C_5F_{11}O_2$, P-$CF_3$), 235 ($C_4F_9O$), 185 ($C_3F_7O$), 169 ($C_3F_7$), 131 ($C_3F_5$), 119 ($C_2F_5$, base peak), 100 ($C_2F_4$), 97 ($C_2F_3O$), 69 ($CF_3$), 50 ($CF_2$), 47 (CFO). IR: 1230 (vs), 1195 (vs), 1158 (vs), 1100 (vs, br), 746 (s, sh), 720 (s, sh), 694 (s, sh) cm$^{-1}$. The FNMR data were reported in Table 5.

Fluorination of tetramethyl orthocarbonate

Tetramethyl orthocarbonate was introduced into the reactor in different manner. Inside the cryogenic reactor the first two zones were packed with a mixture of NaF and copper turnings, and the last two zones were packed with fluorinated copper turnings. Tetramethyl orthocarbonate (2.04 g) was slowly injected into the evaporator and condensed in the first zone by the passage of 60 cc/min of helium flow, while zones 2, 3, 4 were cooled to −100° C. The reactor was then cooled to −120° C. and the fluorination was started using the conditions listed in Table 2. The majority of products stopped in the −78° C. trap on the vacuum-line separation. Final purification on a fluorosilicone column at 0° C. produced 2.63 g of perfluoro tetramethyl orthocarbonate, corresponding to a 49.5% yield.

Perfluoro tetramethyl orthocarbonate, bp. 20.8° C. The FNMR spectrum gave a singlet peak at −59.0 ppm upfield from $CFCl_3$. MS, m/e(fragment ion): 267 ($C(OCF_3)_3$), 201 ($CF(OCF_3)_2$, base peak), 113 ($OCOCF_3$), 85 ($OCF_3$), 47 (OCF). IR: 1170 (vs, br), 1050 (vs, br), 1010 (vs, br), 750 (m), 710 (m) cm$^{-1}$.

Fluorination of tetraethyl orthocarbonate

Tetraethyl orthocarbonate (1.6 g) was handled in an usual way and fluorinated from −100° C. to room temperature (see Table 3). A 2.6 g of perfluoro tetraethyl orthocarbonate was isolated from 2.86 g of crude products. The yield was 56.5% based on the starting tetraethyl orthocarbonate.

Perfluoro tetraethyl orthocarbonate, bp. 80° C. Anal. Calcd. for $C_9F_{20}O_4$: C, 19.58; F, 68.33. Found: C, 19.33; F, 69.05. MS, m/e(fragment ion): 301 ($CF(OC_2F_5)_2$), 163 ($OCOC_2F_5$), 119 ($C_2F_5$, base peak), 100 ($C_2F_4$), 97 ($OC_2F_3$), 69 ($CF_3$), 50 ($CF_2$). IR: 1240 (vs, br), 1100 (vs, br), 850 (m), 750 (s, sh), 725 (s), 675 (m) cm$^{-1}$. The FNMR spectrum consisted of two peaks at −88.3 ppm (—$CF_3$) and −91.0 ppm (—$CF_2$—). The relative ratio was 2:1.

Fluorination of tetra-i-propyl orthocarbonate

Tetra-i-propyl orthocarbonate (1.4 g) was fluorinated using the similar conditions as those for tetraethyl orthocarbonate, except the reaction was initiated at −120° C. (see Table 4). Large amounts of low-boiling products passed to −131° C. on a vacuum-line separation. The GC assay indicated the presence of a number of components, which were inseparable. The −78° C. fraction contained the desired products, from which a mixture of perfluoro tetra-n-propyl orthocarbonate and perfluoro tetra-i-propyl orthocarbonate was isolated in an amount of 0.55 grams. The total yield was 12.8%.

Perfluoro tetra-n-propyl orthocarbonate and Perfluoro tetra-i-propyl orthocarbonate were inseparable under the experiminental GC conditions. Both compounds were thus characterized in a mixture state. The boiling point is around 130° C. Anal. Calcd. for $C_{13}F_{28}O_4$: C, 20.76; F, 70.73. Found: C, 20.97; F, 70.80. MS, m/e(fragment ion): 567 ($C(OC_3F_7)_3$), 401 ($CF(OC_3F_7)_2$, base peak), 213 ($OCOC_3F_7$), 169 ($C_3F_7$), 147 ($OC_3F_5$), 119 ($C_2F_5$), 100 ($C_2F_4$), 69 ($CF_3$), 47 (CFO). The nmr chemical shifts for $C(OCF(CF_3)_2)_4$ are −80.6 ppm (—$CF_3$) and −146.5 ppm (—OCF=). The assignments for $C(OCF_2CF_2CF_3)_4$ are −81.8 ppm (—$CF_3$), −85.3 ppm (—$OCF_2$—) and −130.3 ppm (—$CF_2$—). The relative intensities were consistent with the theoretical value.

TABLE 1

Fluorination conditions for 1,1,3,3-tetramethoxypropane and 1,1,3,3-tetraethoxypropane

| Time (day) | He (cc/min) | F (cc/min) | Zones, Temp (°C.) 1 | 2 | 3 | 4 |
|---|---|---|---|---|---|---|
| 0.5 | 30 | 0.5 | −100 | −100 | −100 | −100 |
| 0.5 | 30 | 1.0 | −100 | −100 | −100 | −100 |
| 0.5 | 30 | 1.0 | −90 | −90 | −90 | −90 |
| 0.5 | 30 | 1.0 | −80 | −80 | −80 | −80 |
| 0.5 | 15 | 1.0 | −80 | −80 | −80 | −80 |
| 0.5 | 15 | 1.0 | −80 | −80 | −80 | −80 |
| 0.5 | 0 | 2.0 | −80 | −80 | −80 | −80 |
| 0.5 | 0 | 2.0 | amb | −80 | −80 | −80 |
| 0.5 | 0 | 1.0 | amb | amb | −80 | −80 |
| 0.5 | 0 | 1.0 | amb | amb | amb | −80 |
| 0.5 | 0 | 1.0 | RT | RT | RT | RT |
| 1.0 | 0 | 1.0 | amb | amb | +50 | +50 |

TABLE 2

Fluorination conditions for Tetramethyl Orthocarbonate

| Time (day) | He (cc/min) | $F_2$ (cc/min) | Zones, Temp (°C.) 1 | 2 | 3 | 4 |
|---|---|---|---|---|---|---|
| 1.0 | 60 | 1.0 | −120 | −120 | −120 | −120 |
| 1.0 | 30 | 1.0 | −120 | −120 | −120 | −120 |
| 0.5 | 30 | 2.0 | −120 | −120 | −120 | −120 |
| 0.5 | 10 | 1.0 | −120 | −120 | −120 | −120 |
| 0.5 | 10 | 2.0 | −110 | −110 | −110 | −110 |
| 0.5 | 0 | 1.0 | −110 | −110 | −110 | −110 |
| 0.5 | 0 | 1.0 | −90 | −90 | −90 | −90 |
| 1.0 | 0 | 1.0 | −80 | −80 | −80 | −80 |
| 0.5 | 0 | 1.0 | amb | −80 | −80 | −80 |
| 0.5 | 0 | 1.0 | amb | amb | −80 | −80 |
| 0.5 | 0 | 1.0 | amb | amb | amb | −80 |
| 1.0 | 0 | 1.0 | RT | RT | RT | RT |

TABLE 3

Fluorination conditions for Tetraethyl Orthocarbonate

| Time (day) | He (cc/min) | $F_2$ (cc/min) | Zones, Temp (°C.) 1 | 2 | 3 | 4 |
|---|---|---|---|---|---|---|
| 0.5 | 30 | 0.5 | −100 | −100 | −100 | −100 |
| 0.5 | 30 | 1.0 | −100 | −100 | −100 | −100 |
| 0.5 | 30 | 1.0 | −90 | −90 | −90 | −90 |
| 0.5 | 30 | 1.0 | −80 | −80 | −80 | −80 |
| 0.5 | 30 | 2.0 | −80 | −80 | −80 | −80 |
| 0.5 | 30 | 2.0 | amb | −80 | −80 | −80 |
| 0.5 | 15 | 2.0 | amb | amb | −80 | −80 |
| 1.0 | 0 | 1.0 | amb | amb | −80 | −80 |
| 0.5 | 0 | 1.0 | amb | amb | amb | −80 |
| 1.0 | 0 | 1.0 | RT | RT | RT | RT |

TABLE 4

Fluorination conditions for tetra-i-propyl orthocarbonate

| Time (day) | He (cc/min) | $F_2$ (cc/min) | Zones, Temp (°C.) 1 | 2 | 3 | 4 |
|---|---|---|---|---|---|---|
| 1.0 | 50 | 1.0 | −120 | −120 | −120 | −120 |
| 1.0 | 30 | 1.0 | −120 | −120 | −120 | −120 |
| 1.0 | 30 | 1.0 | −100 | −100 | −100 | −100 |
| 0.5 | 30 | 1.0 | −90 | −90 | −90 | −90 |
| 0.5 | 30 | 1.0 | −80 | −80 | −80 | −80 |
| 0.5 | 30 | 2.0 | −80 | −80 | −80 | −80 |
| 0.5 | 15 | 2.0 | −80 | −80 | −80 | −80 |
| 0.5 | 15 | 2.0 | amb | −80 | −80 | −80 |
| 0.5 | 0 | 2.0 | amb | −80 | −80 | −80 |
| 0.5 | 0 | 1.0 | amb | amb | −80 | −80 |
| 0.5 | 0 | 1.0 | amb | amb | amb | −80 |
| 0.5 | 0 | 1.0 | RT | RT | RT | RT |

TABLE 5

$^{19}F$ nmr spectra of new perfluorinated polyalkoxy compounds

| Compound | Chemical shift (ppm) |
|---|---|
| $\overset{a}{CF_3O}-\overset{b}{\underset{\underset{a}{OCF_3}}{C}}-\overset{c}{CF_2}-\overset{b}{\underset{\underset{a}{OCF_3}}{C}}-\overset{a}{OCF_3}$ with F substituents | a - 55.6<br>b - 96.6<br>c - 127.0 |
| $\overset{a}{CF_3O}-\overset{d}{\underset{\underset{a}{OCF_3}}{C}}-\overset{e}{CF_2}\overset{c}{CF_2}-\overset{b}{OCF_3}$ with F | a - 55.7<br>b - 56.7<br>c - 86.0<br>d - 97.3<br>e - 128.8 |
| $\overset{a}{C_2F_5O}-\overset{b}{\underset{\underset{a}{OC_2F_5}}{C}}-\overset{c}{CF_2}-\overset{b}{\underset{\underset{a}{OC_2F_5}}{C}}-\overset{a}{OC_2F_5}$ with F | a - 86.6<br>b - 90.3<br>c - 124.8 |
| $\overset{a}{C_2F_5O}-\overset{d}{\underset{\underset{a}{OC_2F_5}}{C}}-\overset{e}{CF_2}\overset{b}{CF_2}\overset{c}{OCF_2}\overset{a}{CF_3}$ with F | a - 87.0<br>b - 82.3<br>c - 88.4<br>d - 92.0<br>e - 127.5 |
| $\overset{a}{CF_3}\overset{b}{CF_2}\overset{c}{OCF_2}\overset{d}{CF_2}\overset{c}{CF_2}\overset{b}{OCF_2}\overset{a}{CF_3}$ | a - 87.0<br>b - 88.3<br>c - 83.1<br>d - 129.3 |
| $\overset{a}{CF_3}\overset{a}{CF_2}O-\overset{c}{\underset{\underset{b}{CF_3}}{C}}-\overset{a}{OCF_2}\overset{a}{CF_3}$ | a - 87.4<br>b - 86.5<br>c - 96.6 |

Equivalents

Those skilled in the art will recognize, or be able to ascertain using no more than routine experimentation, many equivalents to the specific embodiments of the invention described herein. Such equivalents are intended to be encompassed by the following claims.

I claim:

1. Perfluoroalkyoxypropanes of the formula:

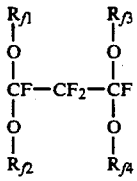

wherein $R_{f1}$, $R_{f2}$, $R_{f3}$ and $R_{f4}$ are the same or different and are selected from the group consisting of $-CF_3$, $-CF_2CF_3$, $-CF_2CF_2CF_3$, $-CF(CF_3)_2$, $-CF_2CF_2CF_2CF_3$, $-CF(CF_3)CF_2CF_3$, $-CF_2CF(CF_3)_2$ and $-C(CF_3)_3$.

2. A compound of the formula:

$$(R_fO)_2CFCF_2CF_2OR_f$$

wherein $R_f$ is selected from the group consisting of $-CF_3$, $-CF_2CF_3$ and $-CF_2CF_2CF_3$.

3. Perfluoro-1,1,3,3,-tetraalkyoxypropane.

4. A compound of the formula:

$$(R_fO)_2CFCF_2CF(OR_f)_2$$

wherein $R_f$ is selected from the group consisting of $-CF_3$, $-CF_2CF_3$, and $-CF_2CF_2CF_3$.

* * * * *

UNITED STATES PATENT AND TRADEMARK OFFICE
CERTIFICATE OF CORRECTION

PATENT NO. : 5,075,509

DATED : December 24, 1991

INVENTOR(S) : Richard J. Lagow

It is certified that error appears in the above-identified patent and that said Letters Patent is hereby corrected as shown below:

Column 10, after line 18 (after Claim 4) insert

---5. Perfluoro 1,1,3,3,-tetramethoxypropane.---.

Signed and Sealed this

Sixth Day of April, 1993

Attest:

STEPHEN G. KUNIN

*Attesting Officer*  *Acting Commissioner of Patents and Trademarks*